United States Patent [19]

Wilhelm et al.

[11] Patent Number: 4,981,993
[45] Date of Patent: Jan. 1, 1991

[54] POLYFUNCTIONAL ETHYLENIC MONOMERS

[75] Inventors: Didier Wilhelm, Hauts de Seine; Alain Blanc, Paris, both of France

[73] Assignee: Societe Francaise Hoechst, Puteaux, France

[21] Appl. No.: 233,545

[22] Filed: Aug. 18, 1988

[30] Foreign Application Priority Data

Sep. 2, 1987 [FR] France ................. 87 12203

[51] Int. Cl.$^5$ ............... C07C 121/30; C07C 69/533; C07C 93/22
[52] U.S. Cl. .................... 560/60; 560/145; 560/183; 549/375; 549/454
[58] Field of Search ............ 560/60, 145, 183; 549/375, 454

[56] References Cited

FOREIGN PATENT DOCUMENTS

| | | | |
|---|---|---|---|
| 0011855 | 6/1980 | European Pat. Off. ............ | 560/183 |
| 0185234 | 11/1985 | European Pat. Off. . | |
| 2533387 | 2/1976 | Fed. Rep. of Germany ...... | 560/183 |
| 61-40279 | 2/1986 | Japan .................... | 549/375 |

OTHER PUBLICATIONS

Synthesis, No. 2, fevrier 1981, pp. 129–130, Georg Thieme Verlag, Stuttgart, DE; H. Stetter et al.: "Additionen von Aldehyden an aktivierte Doppel-bindungen; XXVI. Herstellung und Reaktionen von 1, 1-Diethoxy-2, 5-dioxoalkanen".

Primary Examiner—Mary C. Lee
Assistant Examiner—M. S. Howard
Attorney, Agent, or Firm—Browdy and Neimark

[57] ABSTRACT

The invention concerns new polyfunctional ethylenic monomers of the general formula (I):

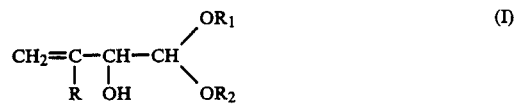

where R=cyano, substituted or unsubstituted acyl, substituted or unsubstituted alkoxycarbonyl or substituted or unsubstituted aryloxycarbonyl; $R_1$ and $R_2$ each represent —$CHR_3R_4$ where $R_3$ and $R_4$ may be identical or different and represent H or an alkyl, alkenyl or aralkyl group. $R_1$ and $R_2$ may, alternatively, together form a radical —$CH_2$—$(CR_5R_6)_n$—$CHR_7$ where n=0 or 1 and $R_5$, $R_6$ and $R_7$ may be identical or different and represent H or $CH_3$.

Particular monomers are: 2-cyano-4,4-dimethoxy-3-hydroxy-1-butene; 2-cyano-4,4-dibutoxy-3-hydroxy-1-butene; 4,4-dibutoxy-2-ethoxycarbonyl-3-hydroxy-1-butene; 2-butoxycarbonyl-4,4-dibutoxy-3-hydroxy-1-butene; 4,4-dimethoxy-2-hydroxythoxycarbonyl-1-butene; 4,4-dimethoxy-2-dimethylaminoethoxycarbonyl-3-hydroxy-1-butene; and 4,4-dimethoxy-2-ethoxycarbonyl-3-hydroxy-1-butene.

9 Claims, No Drawings

POLYFUNCTIONAL ETHYLENIC MONOMERS

The present invention concerns new polyfunctional ethylenic monomers

These new polyfunctional ethylenic monomers correspond to the general formula (I):

$$CH_2=C(R)-CH(OH)-CH(OR_1)(OR_2) \quad (I)$$

wherein:

R represents a cyano group, substituted or unsubstituted acyl group, substituted or unsubstituted alkoxycarbonyl group or substituted or unsubstituted aryloxycarbonyl group, $R_1$ and $R_2$ are identical, each representing a $-CHR_3R_4$ group wherein $R_3$ and $R_4$ may be identical or different and represent a hydrogen atom or an alkyl, alkenyl or aralkyl radical, or $R_1$ and $R_2$ together form a bivalent radical $-CH_2-(CR_5R_6)n-CHR_7$, wherein n is 0 or 1 and $R_5$, $R_6$ and $R_7$ may be identical or different and represent a hydrogen atom or methyl group.

"Substituted or unsubstituted acyl" can mean, for example, an acetyl, propionyl, benzoyl or phenylacetyl radical.

"Substituted or unsubstituted alkoxycarbonyl" can mean, for example, a methoxycarbonyl, ethoxycarbonyl, propoxycarbonyl, butoxycarbonyl, dimethylaminoethoxycarbonyl or hydroxyethoxycarbonyl radical.

"Substituted or unsubstituted aryloxycarbonyl" can mean, for example, a phenoxycarbonyl radical.

"Alkyl" may mean, for example, a methyl, ethyl, n-propyl, isopropyl, n-butyl, isobutyl, 1-methylpropyl or 1-ethylpropyl radical.

"Alkenyl" may mean, for example, an allyl or methallyl radical.

"Aralkyl" may mean, for example, a benzyl radical substituted if required, on the aromatic ring, or a phenethyl radical substituted if required on the aromatic ring.

A more particular object of the invention is a product as defined above characterised in that in formula (I), R represents a cyano or substituted or unsubstituted alkoxycarbonyl group and $R_1$ and $R_2$, when identical, each represent a methyl, ethyl or butyl group. Alternatively, $R_1$ and $R_2$ together form a bivalent radical such as ethylene, trimethylene, propylene or 2,2-dimethyl-1,3-propanediyl.

Among these latter products the invention particularly covers:
2-cyano-4,4-dimethoxy-3-hydroxy-1-butene,
2-cyano-4,4-dibutoxy-3-hydroxy-1-butene,
4,4-dibutoxy-2-ethoxycarbonyl-3-hydroxy-1-butene,
2-butoxycarbonyl-4,4-dibutoxy-3-hydroxy-1-butene,
4,4-dimethoxy-3-hydroxy-2-hydroxyethoxycarbonyl 1-butene,
4,4-dimethoxy-2-dimethylaminoethoxycarbonyl 3-hydroxy-1-butene,
4,4-dimethoxy-2-ethoxycarbonyl-3-hydroxy-1-butene.

Products of formula (I) above can be prepared by methods which are known per se, consisting in reacting the monoacetal of the glyoxal of formula (II):

$$OHC-CH(OR_1)(OR_2) \quad (II)$$

(wherein $R_1$ and $R_2$ have the signification given above) with an ethylenic derivative having formula (III):

$$H_2C=CH-R \quad (III)$$

(wherein R has the signification given above) in the presence of an aprotic alkaline catalyst advantageously selected from the tertiary amines. Preferably the alkaline catalyst is [2,2,2]-diazabicyclo-1,4-octane, hereinafter termed DABCO.

Such methods are described in the following patents: U.S. Pat. Nos. 3,499,024; 3,743,669; 4,652,669; FR Nos. 1 506 132; 2 120 686; EP Nos. 185 234; 196 708.

Products of general formula (I) are valuable polyfunctional monomers which can be used, for example, to prepare polymers.

The following examples are given by way of example and are in no way limiting:

EXAMPLE 1

A solution constituted by:
15.8 g (0.30 mole) acrylonitrile,
25 g (0.22 mole) 90% by weight dimethoxyethanal in methanol,
2.5 g (22 mmoles) DABCO,
6 mg paramethoxyphenol, was agitated for 9 days at room temperature.

The solution was diluted with 150 g diethyloxide then washed with 100 g of 1 N hydrochloric acid and the aqueous phase washed twice with 150 g diethyloxide. The recombined organic phases were washed with water until the washings were neutral then dried over anhydrous magnesium sulphate, filtered and vacuum concentrated. Finally the colourless residual oil was vacuum distilled.

17.58 g of 2-cyano-4,4-dimethoxy-3-hydroxy-1-butene was thus obtained which distilled at 80±3° C. 0.05 mbar.

| Microanalysis | | C % | H % | N % | O % |
|---|---|---|---|---|---|
| $C_7H_{11}NO_3$ | calculated | 53.5 | 7.05 | 8.9 | 30.55 |
| Mol. Wt = 157.17 | found | 53.8 | 7.1 | 8.7 | |

$^1$H NMR in $CDCl_3$ at 200 MHz:
6.12 ppm (m, 2H, $CH_2=$),
4.33 ppm (d, 1H, J=5.8 Hz, $\underline{CH}(OMe)_2$),
4.19 ppm (m, 1H, $\underline{CH}OH$),
3.48 ppm (s, 3H, $\underline{OCH_3}$),
3.47 ppm (s, 3H, $OCH_3$)
2.86 ppm (m, 1H, OH).
$^{13}$C NMR in $CDCl_3$ at 50 MHz:
132.8 ppm $\underline{CH_2}=$,
122 ppm $=\underline{C}$,
116.8 ppm $\underline{C}\equiv N$,
104.9 ppm $\underline{CH}(OMe)_2$,
71.8 ppm $\underline{CH}OH$,
56 ppm $\underline{OCH_3}$,
55.2 ppm $\underline{OCH_3}$.

EXAMPLE 2

0.17 mole acrylonitrile and 30 g (0.15 mole) of 95.5% by weight dibutoxyethanal in butanol were reacted using the method of example 1 to form 22 g of 2-cyano-4,4-dibutoxy-3-hydroxy-1-butene which distilled at 108° C. under 0.1 mbar.

EXAMPLE 3

118 mmoles ethyl acrylate and 10 g (86.5 mmoles) of 90% by weight dimethoxyethanal in methanol were reacted using the method of example 1 to form 4,4-dimethoxy-2-ethoxycarbonyl-3-hydroxy-1-butene as a liquid which distilled at 108° C. under 0.3 mbar.

| | Microanalysis | C % | H % | O % |
|---|---|---|---|---|
| $C_9H_{16}O_5$ | calculated | 52.94 | 7.89 | 39.17 |
| Mol. Wt = 204.2 | found | 52.6 | 7.9 | |

EXAMPLE 4

0.4 moles butyl acrylate and 70 g (0.355 mole) of 95.5% by weight dibutoxyethanal in butanol were reacted using the method of example 1 to form 2-butoxycarbonyl-4,4-dibutoxy-3-hydroxy-1-butene as a colourless liquid which distilled at 130° C. under 0.2 mbar.

| | Microanalysis | C % | H % | O % |
|---|---|---|---|---|
| $C_{17}H_{32}O_5$ | calculated | 64.5 | 10.2 | 25.3 |
| Mol. Wt = 316.44 | found | 64.6 | 10.2 | |

EXAMPLE 5

A solution constituted by:
4.06 g (35 mmoles) 2-hydroxyethyl acrylate,
3 g (26 mmoles) of 90% by weight dimethoxyethanal in methanol,
400 mg DABCO,
2 mg paramethoxyphenol, was heated for 5 hours under agitation, at 70° C.

The solution was subjected to silica chromatography, eluting with a 9/1 vol/vol dichloromethane/methanol mixture and the eluates distilled under vacuum.

4.4-dimethoxy-3-hydroxy-2-hydroxyethoxycarbonyl-1-butene was obtained which distilled at 185° C.±5° C. under 5 mbar.

| | Microanalysis | C % | H % | O % |
|---|---|---|---|---|
| $C_9H_{16}O_6$ | calculated | 49.1 | 7.3 | 43.6 |
| Mol. Wt = 220.22 | found | 49.1 | 7.4 | |

EXAMPLE 6

A solution constituted by:
5.01 g (35 mmoles) dimethylaminoethyl acrylate,
3 g (26 mmoles) of 90% by weight dimethoxyethanal in methanol,
400 mg DABCO,
2 mg paramethoxyphenol, was heated for 120 hours at 50° C. under agitation.

The solution obtained was filtered over silica, eluting with a 9/1 vol/vol dichloromethane/methanol mixture. The eluates were recombined then concentrated under vacuum, and the oil distilled under vacuum. 4.5 g of 4,4-dimethoxy-2-dimethylaminoethoxycarbonyl-3-hydroxy-1-butene was obtained which distilled at 160° C.±5° C. under 5 mbar.

| | Microanalysis | C % | H % | N % | O % |
|---|---|---|---|---|---|
| $C_{11}H_{21}NO_5$ | calculated | 53.4 | 8.6 | 5.7 | 32.3 |
| Mol. Wt = 247.29 | found | 53.4 | 8.6 | 5.6 | |

EXAMPLE 7

400 mmoles ethyl acrylate and 70 g (355 mmoles) of 95.5% by weight dibutoxyethanal in butanol were reacted using the method of example 1 to form 4,4-dibutoxy-2-ethoxycarbonyl-3-hydroxy-1-butene as a liquid which distilled at 120° C. under 0.4 mbar.

It goes without saying that the present invention has been described by way of non-limiting illustration only. Any modification, particularly as regards technical equivalents, may be made without departing from the scope of the invention.

We claim:
1. A polyfunctional ethylenic monomer having the general formula (I):

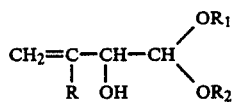

wherein:
R is an alkoxycarbonyl group
$R_1$ and $R_2$ are identical and each represents a —$CHR_3R_4$ group wherein $R_3$ and $R_4$ may be identical or different and is selected from the group consisting of hydrogen atom and alkyl, alkenyl phenylalkyl groups, or
$R_1$ and $R_2$ together form a bivalent radical —$CH_2$—$(CR_5R_6)_n$—$CHR_7$ wherein n is 0 or 1 and $R_5$, $R_6$ and $R_7$ may be identical or different representing a hydrogen atom or methyl group.

2. An ethylenic monomer as defined in claim 1, wherein in formula (I), $R_1$ and $R_2$, when they are identical, each represents a methyl, ethyl or butyl group, or $R_1$ and $R_2$ together form a bivalent radical selected from the group comprising ethylene, trimethylene, propylene and 2,2-dimethyl-1,3-propanediyl radicals.

3. 4,4-dibutoxy-2-ethoxycarbonyl-3-hydroxy-1-butene.

4. 2-butoxycarbonyl-4,4-dibutoxy-3-hydroxy-1-butene.

5. 4,4-dimethoxy-3-hydroxy-2-hydroxyethoxycarbonyl-1-butene.

6. 4,4-dimethoxy-2-dimethylaminoethoxycarbonyl-b 3-hydroxy-1-butene.

7. 4,4-dimethoxy-2-ethoxycarbonyl-3-hydroxy-1-butene.

8. A monomer according to claim 1 wherein said alkoxycarbonyl group is unsubstituted alkoxycarbonyl, hydroxyalkoxycarbonyl or dialkoxyaminoalkoxycarbonyl.

9. A monomer in accordance with claim 1 wherein said phenylalkyl is unsubstituted.

* * * * *